United States Patent
Sorkey et al.

(10) Patent No.: US 9,613,325 B2
(45) Date of Patent: Apr. 4, 2017

(54) DIAGNOSIS-DRIVEN ELECTRONIC CHARTING

(75) Inventors: Alan J. Sorkey, Shreveport, LA (US); Steven Allen Conrad, Shreveport, LA (US)

(73) Assignee: Zeus Data Solutions, Shreveport, LA (US)

( * ) Notice: Subject to any disclaimer, the term of this patent is extended or adjusted under 35 U.S.C. 154(b) by 951 days.

(21) Appl. No.: 13/229,604

(22) Filed: Sep. 9, 2011

(65) Prior Publication Data

US 2012/0004932 A1    Jan. 5, 2012

Related U.S. Application Data

(63) Continuation-in-part of application No. PCT/US2011/042707, filed on Jun. 30, 2011, and a continuation-in-part of application No. 12/827,804, filed on Jun. 30, 2010, now Pat. No. 8,630,842.

(51) Int. Cl.
| | |
|---|---|
| *G06F 15/00* | (2006.01) |
| *G06Q 50/00* | (2012.01) |
| *G06Q 10/06* | (2012.01) |
| *G06Q 50/22* | (2012.01) |
| *G06Q 50/24* | (2012.01) |

(52) U.S. Cl.
CPC .......... *G06Q 10/06* (2013.01); *G06Q 50/22* (2013.01); *G06Q 50/24* (2013.01)

(58) Field of Classification Search
CPC .............................. G06Q 50/02; G06Q 50/22
USPC ................................................ 704/200; 705/3
See application file for complete search history.

(56) References Cited

U.S. PATENT DOCUMENTS

| | | | |
|---|---|---|---|
| 2002/0046346 A1 | 4/2002 | Evans | |
| 2002/0080189 A1 | 6/2002 | Dvorak et al. | |
| 2002/0188896 A1* | 12/2002 | Filteau | G06F 19/3487 714/57 |
| 2003/0146942 A1* | 8/2003 | Helgason | G06F 19/324 705/2 |
| 2003/0220819 A1* | 11/2003 | Burstein | G06F 19/322 705/3 |
| 2004/0122701 A1* | 6/2004 | Dahlin | G01S 7/52098 705/2 |

(Continued)

OTHER PUBLICATIONS

International Search Report and Written Opinion for PCT/US2011/042707, mailed Dec. 27, 2011, 9 pages.

(Continued)

*Primary Examiner* — David Hudspeth
*Assistant Examiner* — Timothy Nguyen
(74) *Attorney, Agent, or Firm* — Fish & Richardson P.C.

(57) ABSTRACT

A computer-implemented method for producing healthcare data records from graphical inputs by computer users includes receiving, on a graphical user interface of a computer system, a user identification of a diagnosis for a patient, the user identification produced by user selection on the graphical user interface; identifying one or more parameters that characterize the diagnosis; displaying on the graphical user interface a plurality of selectable values for particular ones of identified parameters; receiving sequential user selections representations of particulars ones of the values; and generating an electronic medical record representation that represents the identified diagnosis having the selected values for the one or more parameters.

20 Claims, 9 Drawing Sheets

(56) References Cited

U.S. PATENT DOCUMENTS

| | | | | |
|---|---|---|---|---|
| 2005/0107689 A1* | 5/2005 | Sasano | ............... | A61B 6/032 600/425 |
| 2006/0101335 A1* | 5/2006 | Pisciottano | ......... | G06F 17/248 715/211 |
| 2009/0204421 A1 | 8/2009 | Guimaraes | | |
| 2010/0094657 A1* | 4/2010 | Stern | ............... | G06F 19/322 705/3 |
| 2011/0185321 A1* | 7/2011 | Capela | ............... | G06F 3/0488 715/863 |

OTHER PUBLICATIONS

International Preliminary Report on Patentability for PCT/US2011/042707, mailed Jan. 17, 2013, 6 pages.

* cited by examiner

Administered [value:modifier "of"] [modifier] to [base] to treat [value:descriptor] [descriptor]

Modifier = {laceration, fracture, sick}
    Value:laceration = inches; 0-1, 1-2, 2-3, 3-4, 4-5, 5-6
    Value:fracture = simple, compound, greenstick, transverse, oblique, comminuted
    .
    .
    .
    .

DIAGNOSIS-DRIVEN ELECTRONIC CHARTING

CROSS-REFERENCE TO RELATED APPLICATIONS

This application is a continuation-in-part application of and claims priority to PCT Application Number PCT/US2011/042707, entitled "Diagnosis-Driven Electronic Charting", filed on Jun. 30, 2011, and U.S. application Ser. No. 12/827,804, entitled "Computerized Selection for Healthcare Services", filed Jun. 30, 2010, the entire disclosure of which is incorporated herein by reference.

TECHNICAL FIELD

This document relates to mechanisms by which computer users can interact with a computer system to record information about patients in a healthcare system.

BACKGROUND

Healthcare professionals must do much more than care for patients in order to provide patient care. They also need to be part-time administrators, charting the care that has been provided so as to create a complete patient record so that they and other providers may know what treatments the patient has received, and to know which drugs the patient is taking (to prevent harmful drug interactions), for example. They also need to enter information needed for billing purposes, so that their employer can be reimbursed for the care they provide. Sometimes, physicians may spent large portions of their day writing in charts and the like, or may employ transcription services to convert their voice recordings into relevant textual information, and then employ other staff to get that information connected to the appropriate records. Each such step adds expense and the chance for errors to the process. Also, paper recordkeeping suffers from limited or lack of access, illegibility, incompleteness, need for storage, and a lack of safety safeguards.

Electronic records, including electronic medical records (EMRs), electronic health records (EHRs), and electronic billing, have simplified the recordkeeping task and made it more powerful. For example, EMRs can be searched electronically to identify patients in need of certain types of care. EMRs may also be analyzed electronically to identify problems with a patient that may not have been apparent to the team caring for the patient. Also, EMRs allow voluminous data to be stored and accessed for a patient, and for the data to be accessed from any location and my multiple different parties at the same time. Many EMR systems, however, simply attempt to emulate the traditional paper chart. by providing users with templates that are populated with selection boxes, drop-down boxes and text boxes for the entry of findings. Such approaches may require numerous time-consuming mouse clicks or screen touches, diminished operator efficiency and operator fatigue.

SUMMARY

This document describes systems and techniques that may be used for electronically recording notes and other data regarding care that has been provided to a patient in a healthcare setting. The systems and techniques may be used to allow a caregiver to enter information with a minimized number of mouse-clicks, selections and other operations.

For example, a simplified, contextual graphical user interface (GUI) may be provided to a healthcare provider in the form of a plurality of zones, where each zone includes an iconic representation of a healthcare-related object. One zone may include subjects, in the grammatical sense, and other modifiers, while a third zone displays portions of a human body. A healthcare provider may select, e.g., on a touch screen interface, the subject and modifier, and may also select a part of the body on which the particular action was performed. As one example, the subject may be an icon that identifies a diagnosis that a caregiver has already mentally performed and that the caregiver wants to have documented. Selection of the diagnosis icon may result in the automatic display of a variety of other icons that correspond to the diagnosis and that may be subsequently selected by the caregiver to define parameters of the diagnosis. For example, if the diagnosis is typically accompanied by a fever, a thermometer may be shown, and the caregiver may select a number with the thermometer that represents the patient's observed temperature. Other various parameters for the selected diagnosis may also be entered, such as by a caregiver tapping or swiping a finger across icons on a touchscreen. When the parameters have been defined by the caregiver, the selected parameters may be analyzed, and a description of the patient condition and treatment may be generated automatically, including by generating a natural language description.

The techniques described here do not simply deliver a one-size-fits-all diagnosis template that includes all historical elements and physical findings for a diagnosis. Rather, in certain implementations, the provided data is much more granular, with multiple levels that drive medical charting, such as by bringing in all elements of history and physical (body level), elements associated with an organ system (system level), or elements associated with a given organ or exam component (organ level).

In certain implementations, the techniques discussed here may provide one or more advantages. For example, a caregiver often reaches a diagnosis before interacting with a recordkeeping system, so that beginning a recordkeeping process with the diagnosis may be preferential. Specifically, a health care provider often sees a patient and rapidly recognizes the appropriate diagnosis based on the provider's experience, data review, and pattern recognition. The provider may then choose to complete the electronic medical record from the diagnosis both backward (history of present illness, exam, etc.) and forward (treatment plan, disposition, medications. etc). The approach can enable the data entry process for completing the medical record entry to operate more quickly and accurately. In addition, more complete recordkeeping may occur because selection of a diagnosis may then cause all parameters associated with that diagnosis to be presented to the caregiver, and completed by the caregiver.

In one implementation, a computer-implemented method for producing healthcare data records from graphical inputs by computer users is disclosed. The method comprises receiving, on a graphical user interface of a computer system, a user identification of a diagnosis for a patient, the user identification produced by user selection on the graphical user interface; identifying one or more modifiers that characterize the diagnosis; displaying on the graphical user interface a plurality of selectable values for particular ones of identified modifiers; receiving sequential user selections representations of particulars ones of the values; and generating an electronic health record representation that represents the identified diagnosis having the selected values for the one or more modifiers. The values for the modifiers can be displayed adjacent to a representation of the identified diagnosis. Also, receiving the sequential selections may comprise receiving user selections on a touch screen in a single direction from the identification of the diagnosis through the selections of the values. Moreover, at least some of the values can be displayed as selectable icons and at least some of the values are displayed as alphanumeric characters. The method can further comprise, after receiving a selection of a first value of a first modifier, changing values displayed for a second modifier in dependence on the selected first value.

In some aspects, the user identification of a diagnosis is received on an icon having multiple contact zones, and a diagnosis type is selected from multiple different diagnosis types based on a determination of which contact zone for the icon is selected by the user. The method can further comprise applying a syntax to populate a data record for the diagnosis by: identifying at least a modifier and a value selected for the modifier; and constructing a sentence from a template or tree, and adding text for the modifier and the selected value to the template or tree. In addition, the method can include identifying a patient who corresponds to the user selections, and adding a natural language sentence generated using the syntax. And the method can also include receiving a description of a patient complaint, determining one or more diagnoses that address the complaint, and displaying representations of the one or more diagnoses on the graphical user interface.

In another implementation, a computer-implemented system for producing electronic health records from inputs by caregivers in a graphical user interface is disclosed. The method comprises a display controller configured to generate data for displaying selectable icons that represent patient diagnoses, and for displaying values for modifiers of, and that are dependent on, a selected diagnosis; an input processor configured to receive user selections of the diagnosis and values; and a description builder programmed to apply syntactical rules based on the selected diagnosis and selected values to produce prose of a description for a medical action represented by the selected diagnosis and values. The user selections can comprise sequential selections on a touchscreen that identify the selected diagnosis followed by the modifiers. Also, the display controller can be configured to display an icon having multiple contact zones and, and a diagnosis type is selected from multiple different diagnosis types based on a determination of which contact zone for the icon is selected by the user.

In certain aspects, the description builder is further programmed to apply a syntax to populate a data record for the diagnosis by: identifying at least a modifier and a value selected for the modifier; and constructing a sentence from a template or tree, and adding text for the modifier and the selected value to the template or tree. Moreover, the description builder can be programmed to receive a description of a patient complaint, determining one or more diagnoses that address the complaint, and displaying representations of the one or more diagnoses on the graphical user interface.

In yet another implementation, one or more tangible, non-transitory computer-readable storage media are discussed which have stored thereon instructions. When the instructions are executed, they perform operations that comprise receiving, on a graphical user interface of a computer system, a user identification of a diagnosis for a patient, the user identification produced by user selection on the graphical user interface; identifying one or more modifiers that characterize the diagnosis; displaying on the graphical user interface a plurality of selectable values for particular ones of identified modifiers; receiving sequential user selections representations of particulars ones of the values; and generating an electronic health record representation that represents the identified diagnosis having the selected values for the one or more modifiers.

The details of one or more embodiments are set forth in the accompanying drawings and the description below. Other features and advantages will be apparent from the description and drawings, and from the claims.

DETAILED DESCRIPTION

This document describes mechanisms by which an operating system and associated applications may manage interactions with graphical objects that can be viewed by and/or manipulated by a user of a computing device. The mechanisms may display graphical icons to be selected by a caregiver in a healthcare setting, where the selection defines actions taken during a patient encounter and a diagnosis from that encounter. In one instance, the diagnosis may be selected first, which may cause icons to be displayed upon such selection, where the newly-displayed icons represent aspects of the diagnosis and values for those aspects. For example, if the diagnosis is a particular skin condition, the aspects may include the size and location of the visible skin problem, and the icons may enable the identification of an approximate size as well as selection on an image of a human body for defining the location. The information generated from such interaction with the caregiver may be used to automatically generate an electronic medical record for the patient encounter and billing information for submission to a medical billing system.

In certain examples, a caregiver may sequentially select graphical icons that define a subject-verb relationship for treatment of a patient, followed by selecting an area of the patient's body where a diagnosis was made or care was provided.

In other examples, the caregiver can begin by identifying a preliminary or final diagnosis and may then be dynamically presented with various parameters for the diagnosis, so that the user may then select values for those parameters to further define the diagnosis. Based on such user interactions, a system may arrange the ideas represented by the selected icons and values into a phrase or sentence that may be added to an electronic medical record and/or a billing record. Such automatic generation of textual or non-textual (e.g., images) content may permit a caregiver to readily move from one patient to another, and not have to spend extensive time each day translating caregiving actions into records. Also, the caregiver may, when recording is convenient, record the actions close in time to when the actions were performed, thus increasing the accuracy of the records.

A caregiver in certain examples may be presented with a plurality of candidate diagnoses that the system has automatically identified, and the caregiver may select one of the diagnoses to begin a process. As one example, a patient complaint may be provided to a system (e.g., by someone other than a physician). That complaint may have been previously associated with a number of different diagnosis. The physician may then meet with the patient, bring up the list of candidate diagnosis, and then use interactions with the patient to identify which of the diagnoses is the proper diagnosis.

Figure 1A:
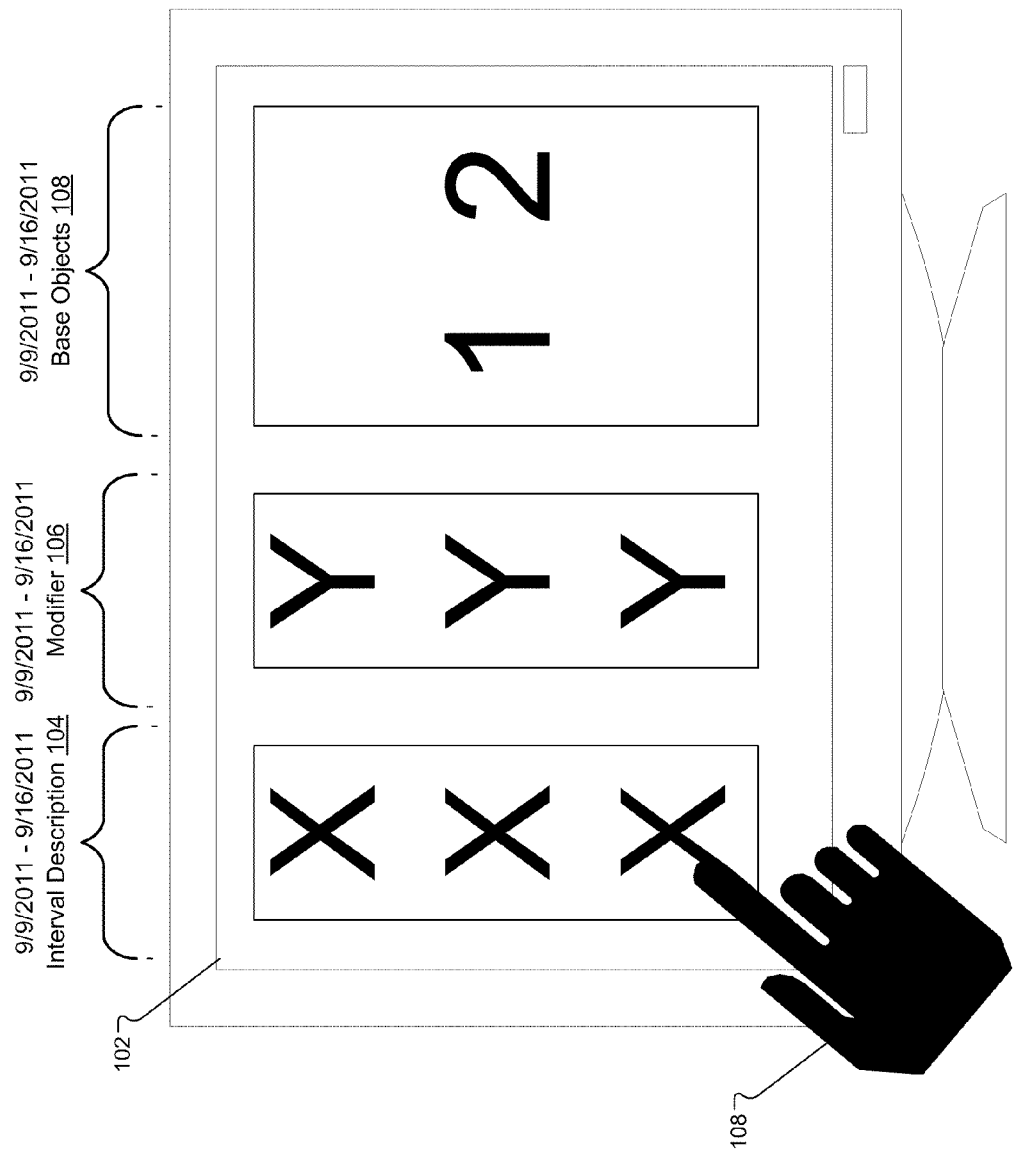
FIG. 1A shows a schematic view of user interaction with a healthcare information input touch screen application.

FIG. 1A shows a schematic view of user interaction with a healthcare information input touch screen application. The figure is intended to show, in broad terms, on-screen graphical elements that may be presented to a caregiver who is seeking to record, to a computer system, information about a caregiving incident. In general, the input paradigm presented in this figure is one of object-action selection, where a caregiver selects an on-screen item that represents some physical aspect of a patient encounter (the object), and also selects an item that represents something that was done with respect to the object (the action). The overall interaction may begin, however, in appropriate implementations, with the caregiver selecting or otherwise identifying a diagnosis for the patient, and then selecting or otherwise identifying various items that are presented as a function of the selected diagnosis.

Referring now more particularly to the features of FIG. 1A, a display 102 is broken spatially into three columns, each of which displays multiple selectable graphical representations, or icons, which are indicated by letters or numbers. A user may select an icon from each column successively to complete a description of an action the user has performed on a patient. Such selection may occur, for example, by the user dragging his or her finger from one side of the display to the other, picking up relevant icons as the user moves. Each of the columns may be initially displayed simultaneously, or certain columns may be added (or altered) only after a selection has been made in another column. Thus, the content in a column may be dynamically selected by the system in a manner that is dependent on selections made elsewhere on the display.

In this example, the columns are ordered by categories, so that each of the icons in a particular column matches the relevant category. The first column 104 shows descriptions of objects that may be relevant to patient care. Such objects may take a variety of forms, such as instruments used to provide care, problems with the patient as determined by a diagnosis, the type of caregiver, and other such object categories.

The second column 106 includes icons for modifiers that are applicable to the first column. Such modifiers may be used to make more specific the general information from the first column 104. For example, if the first column shows icons of medical instruments, the second column may show actions that can be performed with the instruments. Thus a user may first select an instrument that he or she used on a patient (e.g., an adhesive bandage) and may then select an action that he or she performed with the instrument. As shown in more detail below in FIG. 1D, the first column may also show diagnoses, while the remaining columns may show selectable parameter values for parameters that correspond to a previously-selected diagnoses.

The third column 108 shows "base objects," which define where the action was performed. In this example, there are two icons for the base objects, and they may show an image of a man and a woman. A user may then drag from the second column 106 to a location on an image in the third column 108, where the images in the third column may 108 be mapped so that the location on the images that a user selects (e.g., by dragging over from the second column 106, and then releasing to "drop" their description on a particular body part) can be determined and used for later processing.

This process of a user dragging across columns of icons may be used to automatically generate a description in a textual form. In particular, the first column 104 may provide an object or other noun for a sentence, and the modifier may provide a verb, adjective, or adverb for the sentence, and the final selection may provide a subject for the sentence.

The particular arrangement of icon columns may have associated with it a syntax for a particular sentence, where spaces are left to fill in values for the particular items that a user selects. Thus, in the example here, the sentence may map the sorts of objects and modifiers to be shown on the display 102, and the particular values for the icons that the user chooses may be inserted into the sentence. The final sentence may then be a textual equivalent of the graphical thought that the user entered by selecting the particular icons.

The particular sentence structure may be constructed in various manners. For example, the selections by a user may be matched to one or more input templates, in which portions of a sentence are provided statically in the template, and terms that match the user selections are dynamically inserted into the template. Alternatively, or in addition, a tree structure may be used to construct prose from user graphical selections. The tree may be arranged in a variety of known manners, and may implement an appropriate syntax that includes adequate flexibility to permit simplified gesture inputs by a caregiver for a variety of topics.

Figure 1B:
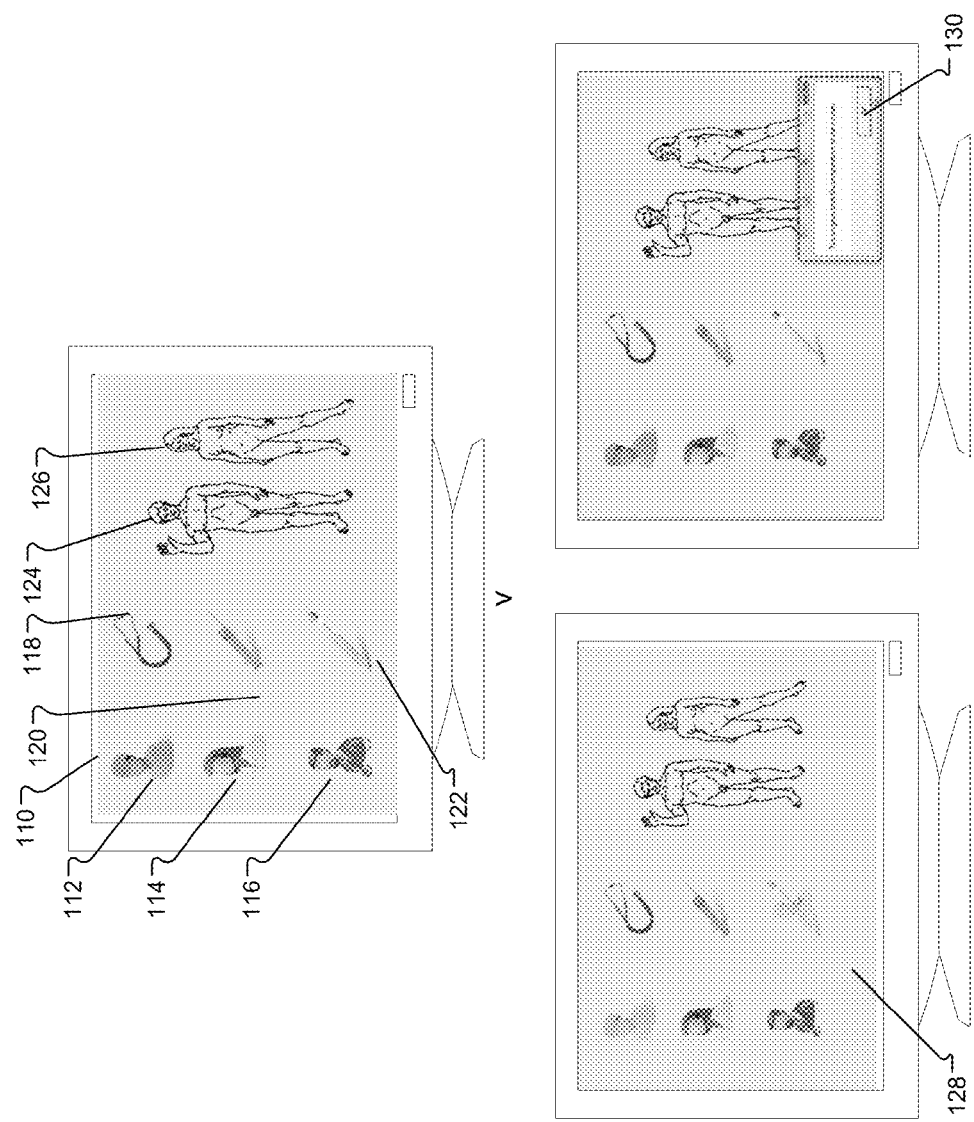
FIG. 1B shows example screen shots for a healthcare information input touch screen application.

FIG. 1B shows example screen shots for a healthcare information input touch screen application. This example has the same form as FIG. 1A, but shows actual data and icons that may be selected by a user. In this example, the first column 110 represents a caregiver type, and the icons show a surgeon 112, a nurse 114, and an attending physician 116. A user may initially touch the display 128 over the icon that represents their role in an organization. This display thus show a paradigm in which selection follows an object-action approach, where the objects here are the caregiver type and items used by the caregiver, and the actions are things that can be done by and with the selected objects.

The second column represents an action that may have been taken on a patient by the caregiver. In this example, the column shows stethoscope 118, syringe 120, and thermometer 122 icons. A user may thus, after selecting their appropriate role, slide their finger across the screen to the right and select the syringe. The syringe icon may be associated, in an ontology for generating a description, with the action of "injection." Likewise, the user may select a thermometer, which may be associated with the term "took the temperature." The user may then continue dragging his or her finger to the third column. As the user drags, the selected icons may be "picked up" by his or her finger so that they appear to move with the finger, such as in a shadowed form, at least momentarily. Also, the relevant icons can be made to disappear from their prior locations as an additional feedback mechanism for the user to indicate that the icons have been successfully selected. Such a situation is shown in the second screen 128.

In a last screen, a description box 130 is shown as appearing on the screen. The user, in the meantime, may have dragged his or her finger to the third column until it reached the icon of the woman, and then may have released the finger from the surface of the touch screen. In this simple example, then, the description box 130 provides the sentence "The surgeon took the temperature of the woman."

In this manner, the user interface may provide a simplified approach by which caregivers can enter information into a computer system to reflect actions they performed on patients, and to have those actions converted to a traditional textual form that can be read on a patient record by other caregivers, and can be processed by various automated systems such as billing systems.

Figure 1C:
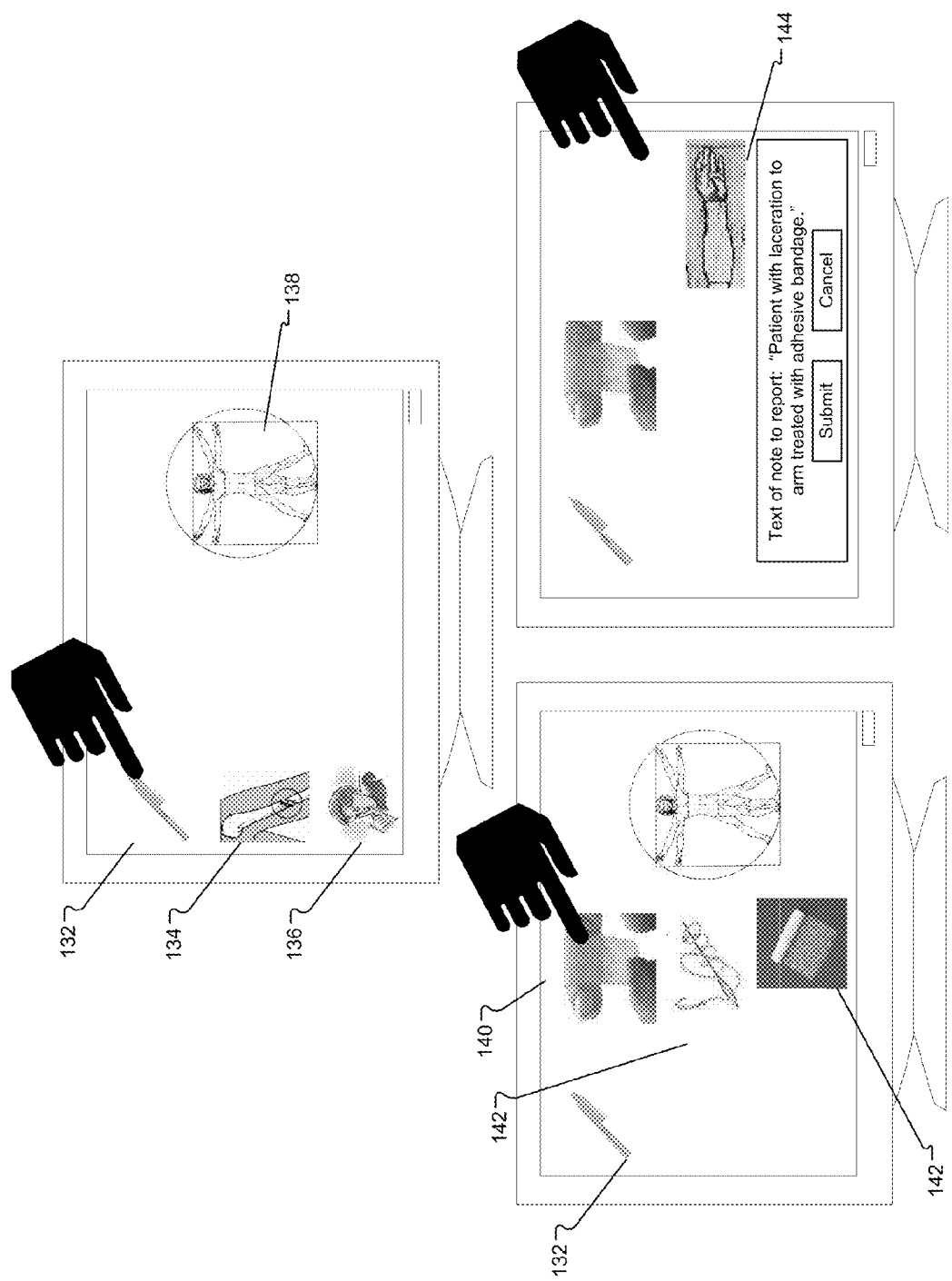
FIG. 1C shows example screen shots for a contextual input application.

FIG. 1C shows example screen shots for a contextual input application. The operations in this figure are similar to those in FIG. 1B, but the icons that appear are generated according to a context of already-selected information from the user. Again, the example is shown in a series of three screen shots that move along progressively in time.

On the first screen, a first column and a third column are initially shown. The third column takes a familiar form of a human body onto which various actions may be dragged to indicate a location where the actions were performed. The first column shows objects in the form of ailments for an incoming patient. In this example, the computer application is being run in a critical care or emergency room area so that common ailments for such an area are shown. The identification of the area in which the application is being run may be made, for example, by the location of the computer, by the identity of the caregiver who has logged onto the computer (e.g., using a password, an ID card, or biometric technology such as a fingerprint swipe).

Additional ailments may be provided for off the screen. In such an example, the user may "scroll" through the other options by swiping his or her finger vertically on the touch screen display, until the relevant ailment appears. In such a situation, the ailments may be sorted from most common to least common, so that the caregiver can find the appropriate icon quickly.

In this example, three ailments are shown. Once, represented by a knife icon 132, covers lacerations to patients who arrive in the critical care center. The second, represented by an icon 134 of a broken arm, represents fractures, which are another common critical care or emergency occurrence. The third, represented by an icon 136 of a person coughing, represents sick patients.

In this example, the user selects the icon 132 to indicate that they treated a patent who had a laceration. Such a selection, by the user pressing on the icon and then moving to the right (a simple press would not indicate a user selection because the user may be starting a scrolling input), causes two changes to the display in this example. First the icons for the other ailments disappear, thus providing an indication that their selection of the laceration icon has been accepted. The user could move back to the left to "undo" the selection, however, and to have the screen return to its original state from the first screen shot.

Second, a middle column of icons has appeared. The column shows icons for actions that modify the selection made in the first column. This middle column was not shown initially because there would have been too many modifiers to cover all of the possible first-column selections. However, once a particular icon is selected in the first column, a smaller number of context-sensitive icons may be generated for the second column. In this example, the generated second column includes an adhesive bandage icon 140, a stitching icon 142, and a gauze bandage icon 142.

Though not shown, other parameters may be display to a user depending on the particular icon he or she chooses. For example, if the user selects the stitches icon, to indicate that they needed to stitch up the initially-selected laceration, the user may be asked to input the number of stitches that were required (e.g., when reimbursement levels are tied to the number of stitches).

In this example, the user selects the adhesive bandage by sliding their finger laterally across it form the location in the first column, on their way to the third column (though they could also tap and pick up their finger for each column). The user has then selected the left arm on the image of the human in the third column to indicate that the stitches were applied to the patient's arm. In response, the icon 138 of the human in the first and second displays has been replaced by a zoomed-in icon 144 of the patient's left arm.

In the final screen shot, the caregiver is also presented with a pop-up box that shows the phrase into which his or her inputs have been translated. In this example, the phrase is "Patient with laceration to arm treat with adhesive bandage." The caregiver is also presented with two selectable controls in the box, so that they can cancel their data entry, e.g., if the sentence is not descriptive of the actions they performed on the patient. They may also choose to submit the description, which may cause the description to be added to the patient's electronic medical record.

A caregiver may be enabled to edit an entry in various manners. For example, a "cancel" or "delete" virtual key may be displayed on a screen, and selection of the button or key may negate the most recently-provided entry. A quick back-and-forth, z-shaped motion with the user's finger, like the motion of a blackboard eraser, may also cause the most recent entry to be negated. Also, a user, after dragging across a full screen of entries and modifiers, may lift their finger and then tap on a desired icon in any row where the caregiver wishes to make a correction. As one example, a physician may miss a desired modifier in a middle column, may nonetheless complete the input motion, and may then go back and tap the correct size, and the generated prose will be modified automatically to match the newly-selected parameter.

Figure 1D:
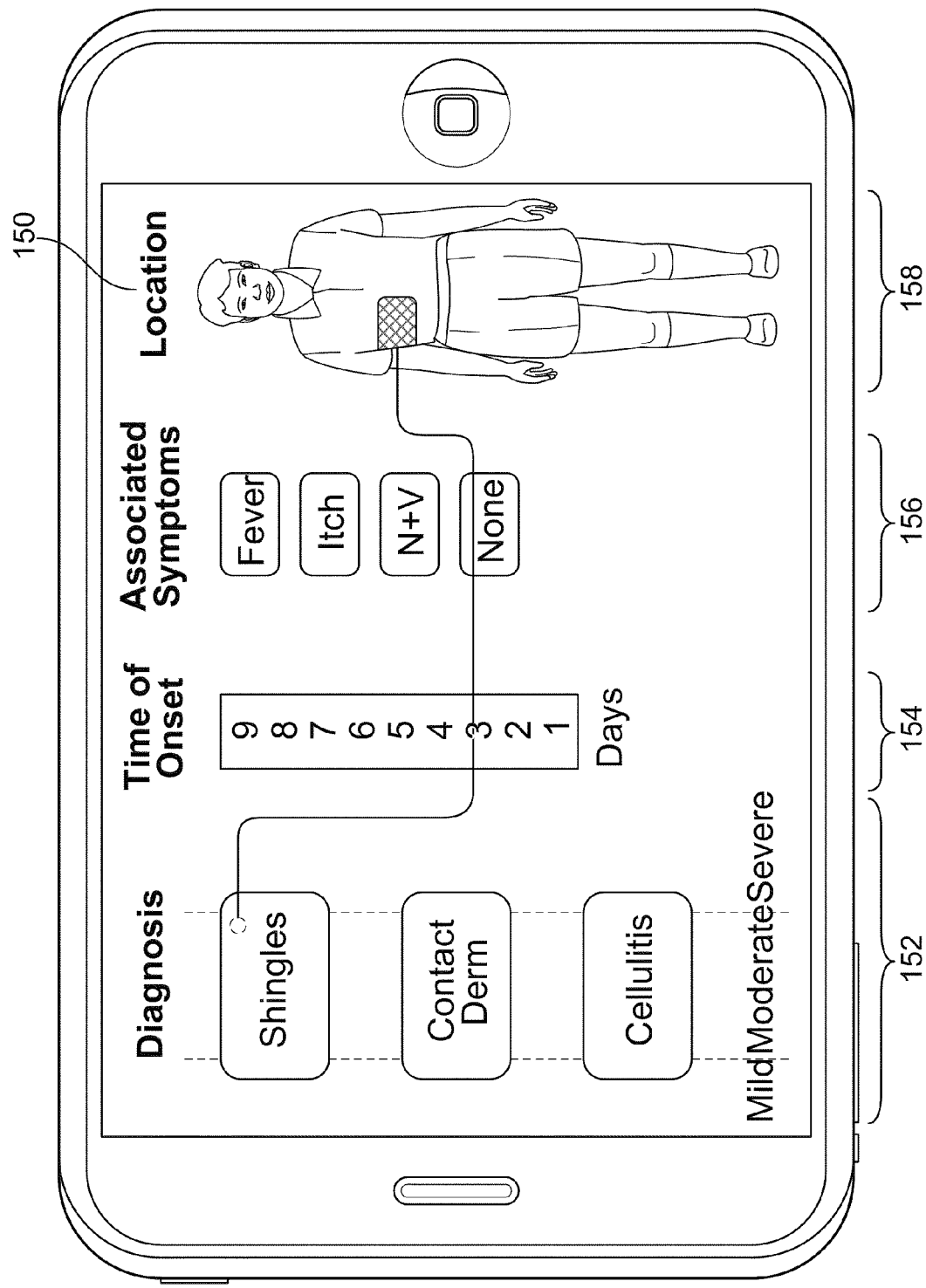
FIG. 1D shows an example tablet screen shot of a diagnosis-driven interface.

FIG. 1D shows an example tablet screen shot of a diagnosis-driven interface 150. Again, this interface is divided into predefined sections for user selection, where, in the example, the sections make up vertical columns in the interface. And again, a user may be expected to provide a complete input by moving from left to right across the display in making selections, such as by tapping sequentially or swiping in one direction sequentially across a touchscreen user interface. In this example, however, the initial selection is of a diagnosis, and the subsequent selections define values of parameters that are predetermined to be aspects of the diagnosis, and are dynamically populated upon the caregiver's selection of a diagnosis.

The first column 152 shows icons for three different diagnoses that a caregiver such as a physician may first select. This paradigm is referred to as being diagnosis-driven because the diagnosis is selected first, and then parameters for that selected diagnosis are provided by the caregiver.

Those candidate diagnoses may have been initially selected for display by the system in response to a user identifying, via a hierarchical arrangement of diagnoses, the type of condition that the patient is facing. For example, at a first level of the hierarchy, the caregiver may have been allowed to identify whether a patient's problem was cardiac related, skin related, ear/nose/throat related, gastro-intestinally related, and the like. In certain circumstances, the caregiver may have then been asked to provide a next level of detail, such as by being shown a menu of additional selections that depend from the first selection, or by being shown an expanding hierarchy of selections and by sequentially selecting more detailed descriptions of the patient's condition.

Eventually, the pool of possible diagnoses will become small enough that they can all be shown on display 150, so that the system shows them in column 152. In this example, the caregiver has selected various identifiers for skin disorders, until the system has determined the possible diagnosis is shingles, contact dermatitis problems, or cellulitis. As a result, the column 152 of icons for those diagnoses has been displayed.

In other examples, the candidate list of diagnoses can be generated based on a complaint from the patient. For example, if the patient complains of itching and a rash, diagnoses of diseases that present themselves, at least in part, with rashes and itching, can be selected. The order of presentation of icons or other indicators for each diagnosis may be based on a determined likelihood that the particular diagnosis is accurate. For example, the sorting may depend on the relative incidence of a disease in a population. The population may be a general population or a particular population, such as based on race, age, or gender, and where the patient's race, age, gender, or other relevant factor can be obtained by the system from historical medical records. The complaint may have been entered into the system by the patient, by an aid to a physician, or by the physician herself. The system may then use defined rules, to identify the most likely candidate diagnoses for presentation to a subsequent caregiver who may then select one of the diagnoses for continuing in the interface shown here.

The icons in the column 152 are selected by the user, and have multi-zone selection capabilities built into them. In particular, a caregiver can represent different input intents by selecting different areas of each of the icons in the column 152, in terms of initially making contact with the touchscreen (or clicking a mouse button) when over the particular area and then optionally beginning a dragging gesture or motion from that point. In this example, the intents are particular modifiers for the diagnoses, where the modifiers are common across each of the diagnoses. To show these modifiers, the display 150 provides labels for them at the bottom of the screen, along with lines that extend up from the labels and pass through each of the respective icons. Specifically, a caregiver can indicate that he or she is diagnosing a mild form of a diagnosis by initially selecting one of the icons on its left edge, a moderate form by initially selected in the middle of the relevant icon, and a severe form by selecting on the right edge. Such mild/moderate/severe dividing of the diagnosis icons may be repeated for many other diagnosis groups that a system may generate so that a caregiver may become accustomed to selecting diagnosis icons in those areas so as to represent the common information.

A second column 154 is displayed here, but may have been hidden until after the caregiver selected the shingles diagnosis (indicated in the figure by a dot in the "severe" zone of the shingles icon). For example, the parameters that are used to invoke the display of the other columns may be integral to the diagnosis that is selected, and are effectively contained within the selected diagnosis icon. Thus, when the diagnosis is selected, the system may access a predefined template that defines information that is needed to be provided with the diagnosis in order to complete a medical record entry for the diagnosis. The template may then be used to populate the rest of the display dynamically, and portions of the template may be displayed, with other portions subsequently displayed after a caregiver selects values for particular parameters in the first displayed portion.

The templates that define what parameters, and values of parameters are to be associated with a diagnosis, may be user-defined. For example, one parameter could be the treatment of the selected diagnosis with medications, and those medications can vary from health care provider to health care provider. As one example, Dr. A may use Amoxil for ear infections and Dr. B may use Zithromax for the same diagnosis.

The column 154 is a parameter of the shingles diagnosis and allows the caregiver to indicate a time of onset in days prior to the current time. In this example, a line is shown from the column 152 through the column 154 to indicate that the caregiver dragged his or her finger from the severe part of the shingles icon through the 3 days value for the time of onset parameter.

Likewise, a third column 156 indicates symptoms that may be associated with the malady in the patient. Such symptoms for shingles commonly include fever, presence or absence of itching, and nausea and vomiting. Upon the caregiver selecting the shingles icon, the system may have looked up the parameters that have previously been identified as being related to shingles, and may have gathered data automatically to populate the column 154 and the column 156. In this example, the line—flowing from the left to the right to indicate user dragging on a touchscreen from left to right—shows that the caregiver identified no corresponding symptoms for the shingles.

Finally, a fourth column 158 shows a graphic of a simplified patient. Such a graphic may be presented as the final column for most sorts of diagnoses, and its display may be triggered by a flag that is set for the particular diagnosis that indicates whether the diagnosis has a body-position component. For example, diagnoses relating to skin condition or pain obviously relate to a position on the body. Other diagnoses, such as mental disorders, may not have such a correlation, so that column 158 would not be invoked for them.

In this example, the caregiver has continued dragging to a point in the right midsection of the virtual patient shown on the display 150. In this manner, the caregiver can easily indicate where on the patient's body the shingles is manifesting itself.

In certain implementations, an input like that just discussed can be repeated by a caregiver in various manners so as to save effort in having to re-enter data. For example, if a patient has two maladies, the caregiver may—after sliding her finger across the display to define the first malady—pick up her finger and then start dragging again at a point to the right of the column that is common for the maladies. For example, if a patient has evidence of shingles in two parts of his body, the caregiver could drag fully across the display as shown here, then lift up her finger and put it back down between column 156 and column 158, and then drag again onto the second part of the body where it occurs. If that other instance of shingles appeared four days prior, the caregiver could pick up her finger after the first entry, and put it back down on the display between column 152 and column 154, drag through the four, drag through the none box, and drag onto the relevant part of the body.

Separately, a caregiver may backtrack on any particular entry by keeping her finger in contact with the display and dragging back right-to-left through the column she wants to reset. The display may provide indications that such inputs—both to select a value for a parameter and to re-set it—have been registered with the system. For example, when a value is set (e.g., upon determining that a user has dragged left-to-right all the way through a particular column and over a particular value), the particular value may be visually highlighted, such as by changing its color to a color that is brighter than it had before the selection and brighter than the colors of the other values in a column. In addition, haptic feedback may be provided, such as by a computing device that is showing the display being caused to vibrate slightly as entered values are recognized by the device.

The parameters in columns 154 and 156 may be ordered by a developer or user of the application so as to minimize the level of backtracking and reentry that may be required when a user wants to duplicate a prior data entry or correct such an entry. For example, the parameters may be ordered from most general to most specific from left-to-right under the assumption that more general categories will not need to be changed as often in a reentry, and thus should be farthest from the final input point at the right of the display. Such ordering may also occur automatically. For example, a system may keep track of corrections or re-entries that have been made, and if the user or multiple users in a group are observed to backtrack through two columns more often than through only the rightmost column, the order of the columns can be reversed so that the most-corrected column is closest to the data entry finish on the right.

A caregiver may also be provided with mechanisms to bring up prior diagnoses that were made for other patients as a form of templates for a current data entry session. For example, once a diagnosis has been selected, the system may gather data for the last n times that the caregiver entered the same diagnosis (where n is an integer number). Reduced-sized reconstructed screen shots may then be displayed to the caregiver along with a user interface to let the caregiver scroll through such shots and select one of them to use. That data entry example may then replace the blank one on the display, and the caregiver can use the back-tracking techniques discussed above to make amendments to it so as to align it with the current patient's actual medical condition.

In other implementations, context-dependent assistance in making or confirming a diagnosis may be provided to the caregiver. For example, one or more items such as HTML documents can be associated with each of the selectable icons in column 152 and/or with particular diagnoses that can be represented by such icons. The items then may be presented to a user, such as if a user selects a "help" icon next to the corresponding diagnosis icon or button. For example, selection of such a "help" icon next to the shingles icon can cause an image of shingles to be shown, and could also bring up textual descriptions of shingles and example treatments for shingles.

As another diagnosis-driven example that starts with a patient encounter, the patient may complain: "my eye is red." The physician may then walk into the room and within a few seconds, may see that the patient has a sty (or sometimes stye). The user may have entered the complaint into the system, or the physician may type or state into the system "red eye" as a simplified description of the problem, even though the physician knows that the diagnosis will be for a sty. The system shown here would then populate the first column 152 of potential diagnoses with the most common causes of a "red eye" such as conjunctivitis, sty, episcleritis, scleritis, iritis, corneal abrasion, corneal foreign body, and glaucoma. If the correct diagnosis is not listed, the provider can simply speak the diagnosis or select if from a search or a list of all diagnoses.

Also, if the provider is not sure about the diagnosis, the provider can process an icon next to icons for each of the potential diagnoses in order to obtain more information about the diagnosis or diagnoses. For example, a photo line up may be displayed of an eye that suffers from each of the diagnoses so that the physician can compare the patient's condition to such standard condition. Similarly, a textual description of a selected diagnosis may be provided so that the provider can confirm whether his or her initial view of the diagnosis is correct.

In this case, when the diagnosis of Sty is selected, the following variables/modifiers would be presented as a row of columns to the right of the diagnosis column on the left of the screen:

Time of Onset of the symptoms (hours, days, weeks)
    Severity of the symptoms (mild, moderate, severe)
    Associated symptoms (fever, itching, drainage, decreased vision, headache)
    ROS (Review of Systems—not related to the chief complaint)(top of list would be "Other systems reviewed and are negative, but a brief list would follow to list major systems such as neurologic, musculoskeletal, abdomen, respiratory . . . )

Any one of these or any combination may be displayed, where each may be displayed in a column or other defined area (e.g., if there is only room for three columns, the time of onset and severity can be displayed in vertically stacked arrangement in a single column, within outlined areas).

The provider may then select the relevant parameters to fill out the diagnosis using the drag-thru process, including by breaking contact with the display at the relevant location in the eye of the generic patient in column 158 where the sty is located. The system can generate an entry for a medical record using the selected parameters, in manner discussed above and below.

The description may read, for example:

"HPI (History of present illness) Miss Jones, a 23 year old female, presents to the ABC clinic at 9:08 on Jun. 23, 2011 with a chief complaint of 'my eye is red.' The symptoms started gradually 3 days ago and she rates them as moderately severe. She complains of some drainage from the affected eye but no decrease in her vision and no fever."

"ROS (Review of symptoms) Other systems have been reviewed and are negative."

"PE (Physician Exam) Eye Exam: The patient has a 3 mm sty on the upper lid, medial border, of the right eye. Pupils are normal, eye movement is normal, conjunctiva are normal, not red. The other eye is normal."

"MDM (Medical Decision Making). The patient has a simple sty and will be treated with antibiotics both orally and topically and given analgesic relief."

"Differential Diagnosis List: Same as the initial list for starting the process above"

"Diagnosis: Stye, right upper eyelid, with ICD10 code listed"

"Disposition: Home"

"Work Excuse given for 3 days"

"Referral given to eye doctor in 3 days if not healed, sooner if getting worse or return to the clinic/ER"

"RX given for oral antibiotic, topical antibiotic, pain medicine"

"Discharge instructions given for the dx of Sty and how to care for the condition."

Yet another example involves more complex diagnosis, with an expanded and more complex differential diagnosis, and irrelevance of discharge instructions or follow-up care because the patient is admitted. Also, as a consult, an admitting physician may be called to admit the patient, and an admitting diagnosis and level of care may involve placement in observation versus admission to the hospital and level of care, general medicine bed, telemetry bed, stepdown bed, ICU bed, OR, cath lab. Suggested admission orders can be generated to streamline the process and reduce errors.

The entry of such parameters for the various factors for the diagnosis may thus occur over multiple pages. Also particular parameters may simply not be displayed, such as a parameter to select values for discharge instructions once a selection for another parameter indicates that the patient will not be discharged.

A record generated form such an encounter may take the form of:

"67 year old male arrives from home via 911 EMS with the chief complaint of 'I'm short of breath.' The symptoms started gradually 3 days ago and became much worse at 4 am this morning when he was awakened from sleep and could not catch his breath. He states the shortness of breath is severe and denies any chest pain but does have progressive edema to both lower extremities worsening over the last 3 days. There has been no fever or nausea or vomiting. He does have a non-productive cough for the last 24 hours. Does feel that his heart is 'racing away.'"

Review of Systems:
  Eyes: no blurred vision or eye pain
  ENT: No nasal congestion or nose bleed or decreased hearing
  Neck: No neck pain or swelling.
  Lymphatic: no swollen glands
  Neurologic: No headaches, weakness, dizziness or fainting, no confusion
  Cardiac: No chest pain. Positive as in HPI for palpations
  Respiratory: Positive as in HPI for shortness of breath but no hemoptysis.
  Abdomen: no abdominal pain, nausea or vomiting or diarrhea
  Musculoskeletal: No back pain, no muscle aches. Positive for leg swelling.
  Psych: No depression, no suicidal or homicidal ideation. Insight is normal.
  Skin: No rashes or lesions. Positive for clamminess 6 hours ago.
  Other systems reviewed and are negative.

"PE: General: the patient is well developed and well-nourished and appears in acute distress and is agitated. Vital signs are reviewed and are remarkable for marked hypertension, rapid heart rate and low oxygen saturation."

"HEENT: Pupils are normal, equal. Lids and lashes are normal, no redness or edema. Hearing is normal. External nose and ears are normal. Mouth and throat are normal, some teeth are missing and a partial bridge is in place.
  Neck: Supple, full range of motion without pain. Thyroid is palpated and is normal. Trachea is midline and mobile. Jugular venous distention is present to the angle of the jaw bilaterally.
  Cardiac: irregularly irregular with rate of about 160 beat per minute. No murmur is heard.
  Lungs: rales are heard ½ way up the chest on both sides. No wheezes are heard. Breath sounds are heard thru out the chest.
  Abdomen: soft, non-tender, no masses, no hernia felt.
  Back: normal
  Genitals: normal
  Extremity Exam Pulses are intact and equal. 2+ pitting edema is present from the knees thru the feet but is equal bilaterally. Calves are non-tender and without cords."
  Neuro: Alert and oriented times 3, agitated due to obvious respiratory distress.
  Psych: Normal affect, normal responses, good insight.
  Skin: cool and clammy. No rashes or lesions are noted.

"Medical Decision Making: Results of tests that confirm the diagnosis and treatment plan offered."

"Differential Diagnosis: extensive list provided."

"Disposition: Admit to ICU in guarded condition to Dr. XYZ."

"Condition: Guarded"

"Admission orders generated to be signed electronically."

Particular parameters and values for those parameters have been discussed in this example. The parameters that are shown may change from diagnosis-to-diagnosis and from activity-to-activity. For example, the parameters may include one or more of the following:
  Chief Complaint
  History of Present Illness
  Review of Systems
  Past medical history
  Past surgical history
  Social History
  Medication List
  Allergies
  Vital Signs
  Physical Exam
  Test Results
  Medical Decision Making
  Disposition
  Treatments
  Prescriptions
  Follow up Care As one additional example, a patient may complain "I have a rash". The provider may then evaluate the patient, immediately determines by pattern recognition that the "rash" is the Shingles (Herpes Zoster), and may ask the questions that relate to that diagnosis. The provider can then "document" the encounter using diagnosis driven charting. For example, the term "rash" may have previously been entered, or the physician may enter it, and the system may present the following candidate diagnoses: Contact Dermatitis; Shingles; Tinea; Scarlet Fever; Viral Rash; Atopic Dermatitis; and Non-specific Dermatitis. Using statistical figures, the candidates may be sorted from most likely to least likely (and, e.g., the patient's age may be consulted so that a Shingle diagnosis climbs in likelihood for older patients). The system can then present icons for each such candidate diagnosis. If the system does not present the needed diagnosis on the first attempt, the physician can either use a search feature or speak the diagnosis and have it appear in the left hand column to begin the diagnosis driven charting process.

The physician may then drag through—e.g., from left to right—appropriate modifiers for that particular diagnosis (the number of and complexity of modifiers being dependent on the diagnosis). In this example of Shingles, the modifier columns could be:

Time of Onset (having values of an adjustable numeric scale, on a slider UI, starting with days but moveable in any direction (to seconds, hours, weeks, months, years, etc.).

Intensity/Severity (scale options would be to use the approved "pain scale" of 0-10 or mild, moderate and severe.

Associated symptoms such as fever, nausea, itching, pain, burning.

After dragging through selections of values for these parameters, the physician may end the input by "depositing" the diagnosis with all selected attributes in the correct anatomic location of the target anatomy model (in the case of Shingles, the model will be automatically displayed in nerve dermatomes as that is how the rash presents).

When the physician has completed such an input process, the appropriate areas of the medical record may be populated using the values of the parameters that the physician entered, such as: "HPI to read, 23 year old male presents to the emergency department with the complaint of 'I have a rash.' The rash began 3 days ago, is described as 'severe' and is associated with severe pain, itching but without fever. The patient has no complaints of nausea or vomiting." Certain positive statements in this textual description may be made based on the lack of user input (e.g., by the physician identifying itching but not identifying any value for a fever).

The physical exam in this example could populate with: "A band like rash of vesicles on a red base is present in left T12 dermatome." The Medical Decision Making can populate with: "The rash is consistent with Shingles." The Diagnosis can populate with "Shingles" The Disposition can populate with "home", work excuse/school excuse for 3 days. And the discharge instructions can be selected for the diagnosis of Shingles. Moreover, prescriptions can be populated with "1. Benadryl for itching 2. Acyclovir for the rash 3. Prednisone Taper for the rash 4. Lortab for pain." Finally, the system may also assign and calculate "bullets" or points that coders use to determine the level for billing purposes.

The examples just discussed generally relate to using a diagnosis to control the population of a particular screen that is associated with a single patient encounter or clinical observation. The same techniques may also be used to populate a clinical record at various different levels. For example, an entire clinical record (history, physical findings, imaging findings, etc.) may be populated in this manner. In addition, a record for a particular organ or organ system of a patient (e.g. cardiovascular exam findings) may also be populated across multiple screens and sets of user inputs. Particular details can also be provided automatically to a medical record in such a situations, and the user may have the opportunity to modify such default information before saving the information to the medical record.

The particular order for the entry of information shown in the examples above may also vary, and a user may remove entries that have already been made. Such entry may occur, in certain implementations, using a sequential selection on different defined areas of a graphical user interface, including by a user dragging their finger across a touch screen. For example, a user may bring up a list of symptoms that would be considered to be parameters of a diagnosis in the techniques described above, may select a particular symptom, and may then select a diagnosis. In certain circumstances, multiple symptoms that correspond to one or more parameters (and thus to one or more columns of the user interface described above) may also be specified by a user, such as by first selecting in one column to see skin-based symptoms, then selected "rash" as a particular symptom, and then selecting an area of the body. The user may then select, for another parameter, a list of more systemic symptoms and may identify the patient's temperature as a particular systemic symptom, and may specify the temperature (such as by selecting a number form a scrollable list, e.g., 98.6, 98.8, 99.0, 99.2, etc.). In such a situation, a list of diagnoses may be displayed in another area of the display (e.g., the first column) and may be updated as the user enters more parameters. Such an approach may thus permit dynamic selection of diagnoses and medical care parameters, so as to provide maximum flexibility to a user interacting with such a system.

The user may also backtrack and remove selections of particular entries, such as by sliding a finger back substantially over a path the user traced in making the selections that are to be vacated. For example, if a user is tracing from left-to-right across multiple columns of selections on a display, the user can move back right-to-left across a column to vacate its selection. In certain circumstances, a user tracing back over a previously selected item in a column may cause the selection of the item to be vacated, whereas a user tracing back over the column in a place other than the selected item will not—so that a user can then sweep again in the initial direction across another item in the column so as to select two values for the particular parameter. For example, if a column shows a list of skin symptoms, the user may swipe across "rash", then circle back to the first side of the column and move across the column again on "swelling." The user may then drag onto a patient image to indicate where the rash and swelling are co-located. If the rash and swelling are in different locations, the user may also swipe across "rash," then swipe to an area on the body where the rash is located, may circle back across the column and select "swelling" and then swipe onto the body in the location where the swelling has been observed. And again, with the other operations discussed above, the selections may be made sequentially, either by (a) swiping with continuous contact with a touchscreen or while holding down a mouse button or other selection mechanism, and the completion being indicated by a user release; or (2) tapping or clicking individually on each item in sequence (e.g., clicking on a diagnosis in a first column, then clicking on a particular value of a parameter that is shown after the first click, then clicking on a particular value of a parameter in a second column or area and may be dependent on the first selection and/or the second selection, and then clicking on an area of a patient body on the display.

The systems and methods discussed here may also interact with a caregiver who has made a "finding" but not yet a complete diagnosis. A finding may be a conclusion reached from physical examination (e.g., visually, by auscultation, palpation, smell, percussion, succession, and ballottement) but that falls short of a diagnosis. For example, a physician may make certain initial conclusions when first examining a patient, but may order additional tests before the physician can make a final diagnosis. As a particular example, a patient may complains that "the left side of my face is weak". After a physician conducts an examiner, the physician may confirm the patient's statement and make a finding of left-sided facial weakness. If it is a simple case, the physician may immediately make a diagnosis of a Bell's Palsy or facial nerve weakness and can document the diagnosis using the various techniques discussed above.

But if the case is complex (e.g., the patient has alerted mental status, cannot cooperate with exam, etc.) the physician can use techniques like those discussed above to document the finding in a manner similar to how the physician can document a diagnosis. For example, the physician may first contact the left side of the face of a patient displayed on a touch screen, and may then identify facial weakness as a finding. Such an identification may, in certain circumstances, cause additional parameters for the finding to be displayed, and the physician may then selected certain values to provide for one or more of the displayed parameters. Again, the input may be via sequential touch input (including sliding input) across spatial areas on a touch display so as to provide the relevant information. A diagnosis may also be documented for a patient chart in such a situation, such as in the form of: "Left Sided Facial Weakness/Palsy, Unknown Cause, Bell's Palsy versus Stroke".

Figure 2A:
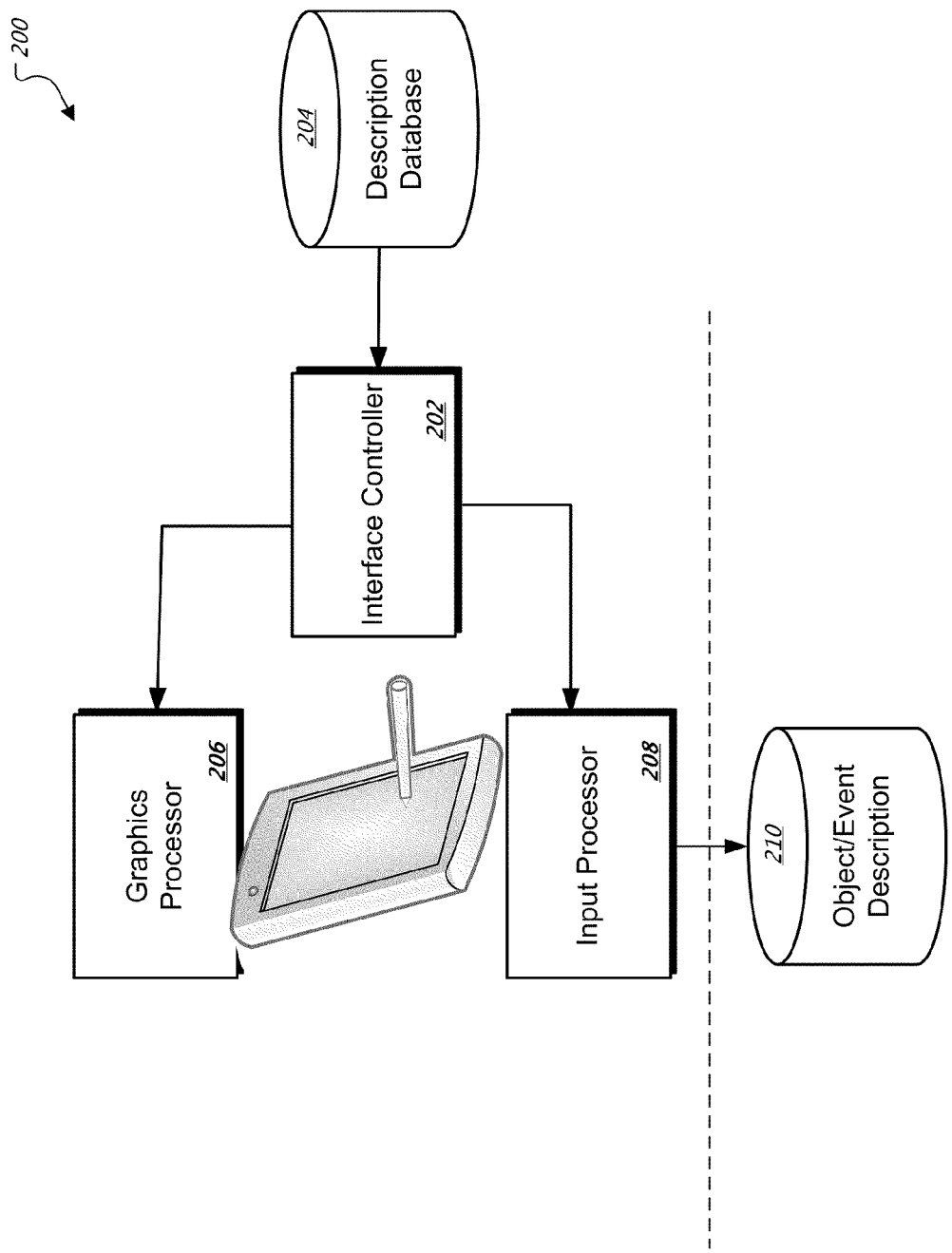
FIG. 2A is a block diagram of a system for providing interaction with a user input.

FIG. 2A is a block diagram of a system for providing interaction with a user input. This is a relatively simple diagram that shows major components of a system for converting user inputs on a graphical interface into textual outputs that describe actions performed on a patient.

A standard touch screen device is shown at the middle of the figure, and is surrounded by components that may be executed on the device, on a separate device such as a server, or a combination of the two. A graphics processor 206 is shown serving the device, and may be a combination of software and hardware components that are programmed to generate displays like those shown in FIGS. 1B and 1C. The graphics processor in particular may select icons to be associated with particular categories relating to patient care, and may arrange the icons in an appropriate manner, grouped in the categories, so that a user may be presented with an intuitive mechanism by which to select particular icons to describe their actions.

An input processor 208 is responsible for receiving information about where selections on a display have been made (e.g., via a touchpad or touch screen), and to coordinate the locations of the selections with information that is currently shown on the display. Thus, for example, the input processor may determine whether a user selected a particular icon, and may provide such information to other components of the system 200.

The graphics processor 206 and input processor 208 may be part of, or otherwise managed by, an interface controller 202. The interface controller 202 accepts information about icons or other graphical elements to be displayed, which may be stored in the description database 204. It may also accept other information, such as the categories within which each element belong, the display coordinates for an element, the relative display position of an element in a category (which may be based on the frequency with which the element is selected in a particular context or environment) and object/event descriptor terms that are associated with each element.

An object/event description may be generated by the system as an output from a user selecting particular elements (via icons) on a display of the device. The object/event description may be simply a textual, prose conversion of the graphical concepts that a caregiver selected on the screen, like the textual descriptions shown in FIGS. 1B and 1C. Other forms of the textual description may also be provided, and they need not take the form of a full, or grammatical, sentence.

Figure 2B:
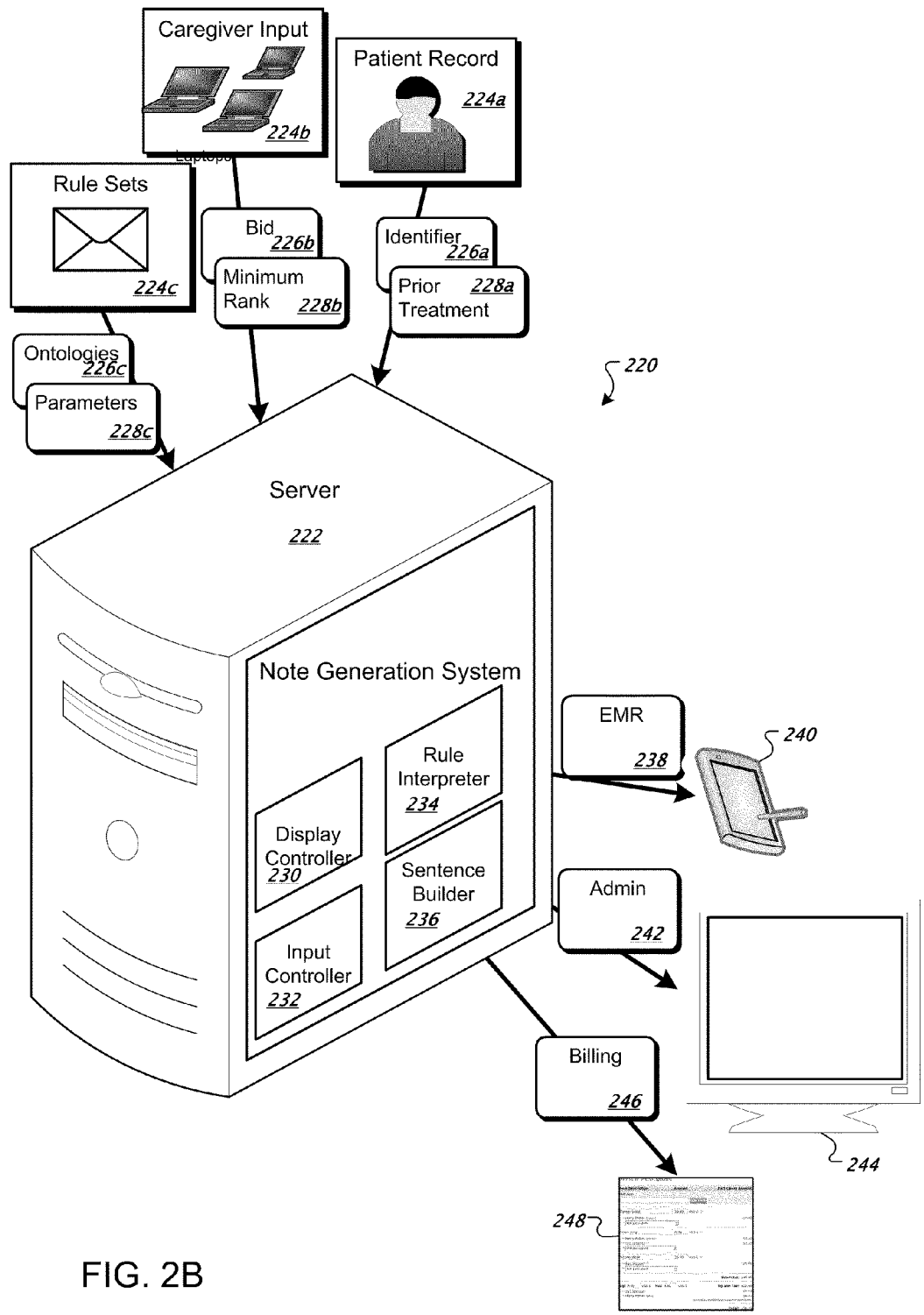
FIG. 2B is a block diagram of a system for generating healthcare notes from caregiver inputs.

FIG. 2B is a block diagram of a system 220 for generating healthcare notes from caregiver inputs. In general, the system 220 responds to graphical inputs from a user, such as the dragging of a user's finger or other form of pointer (e.g., a stylus) such as dragging across icons groups that represent medical objects (e.g., body parts of a patient, or medical instruments) or medical actions or conditions to be performed on the objects, or observed from the objects.

The system 220 in this example centers around server system 222, which may be implemented as one or more computer servers that interact, over a network, such as a LAN or WAN, and/or the internet, with client devices which users of the system 220 employ. The server provides simplified interaction for such users, and translation of user inputs into other forms (e.g., from graphical dragging to a textual description with or without images or other content and meta data). Various structural components within a note generation system of the server system 222 permit such interaction. For example, a display controller 230 may be responsible for providing data used to generate a graphical display of information for a user who is employing the system 220. Such as display may be similar to the displays depicted in FIGS. 1A to 1C. The display controller may access a variety of information sources, including patient records 224a, graphical resources such as libraries of icons, rules and instructions for selecting particular icons, and other such data sources.

An input controller 232 may operate in cooperation with the display controller 230 in order to interpret user input to the system. The input controller may interpret user inputs, including by coordinating inputs at a certain location on a display screen, with information that is displayed on the screen. Thus, for example, the input controller 232 may determine when a pointer that is in contact with a touch screen is over a particular icon or group of icons, and may take programmed actions in response to such determinations.

The particular components discussed here are shown for convenience as being located on the server system 222, though the components may also be located wholly or partly on a client device. For example, using asynchronous JavaScript and XML techniques, a client device may track user interaction with a document and may report to a server system such as server system 222 when a user takes relevant action with respect to the document. The server system 222 may then process such input and may respond asynchronously with information that the client may need. As one example, the server system 222 may provide to a client device mark-up code and other code such as JavaScript code that is integrated with the mark-up code, so as to generate a display like that in FIG. 1B. The code may track a user's sliding of their finger across the various groups of icons, and may wait until the user has identified a relevant number of the icons, before sending such information back to the server 222. At that point, the identification of the icons selected by the user may be transmitted, and the server system 222 may then be responsible for interpreting the user input, for storing information in a central repository about it (e.g., by updating a medical record) and by providing feedback to the physician (e.g., showing a draft addition to the patent medical record, or otherwise confirming that the user's input has been processed).

A rule interpreter 234 and sentence builder 236 operate together to turn user input that occurred in a graphical manner into a form that can more easily be stored and referenced later by the user who entered the data or by other users. The rule interpreter 234 receives a variety of rule sets 224a, which may define ontologies 226c and other parameters 228c. For example, a rule set 224c may define that, when a certain medical device is selected, only certain actions may be identified for that device, so that a user employing the interface of FIG. 1B would be limited in his or her subsequent choices once he or she selected a particular medical device. Such relationships may be defined by one or more ontologies 226c, which defines a representation or model of the relationship between various graphical components that a user selects in a graphical system, and certain words or phrases that may be represented by such selections. Thus, the rule interpreter 234 breaks apart the particular selections made by a user, and the sentence builder puts them together to form a natural language description of the observation or other action that a user enters into a system. Such description may in turn be added to the patent's electronic medical record 238 or accessed from other points.

Various inputs are used by the system 220 to generate graphical displays for interacting with a user and for translating the user's interaction with such displays into other forms of input that can be stored and referenced by other portions of the system 220. As mentioned, for example, rule sets 246c may be provided to the system 220 and can define how user input is translated. Such rules may be provided by a third-party or can be programmed by the users themselves (e.g., by tracing paths through icons and then providing structured outputs that are to correspond to such paths).

Caregiver inputs 224b may also be received, such as via input controller 232. The inputs 224b may take a variety of forms. For example, a user may provide an identifier 226b both for themselves and a patient. User identification may occur via a badge the user wears or via one or more biometric checks (e.g., fingerprint, hand or eye scan, etc.). Patient identification may occur simply by the terminal a user is employing (e.g., the system knows that a terminal is adjacent patient X's bed), by the user typing in information to identify the patient, or by other such mechanisms.

The various inputs that a user may provide may, in appropriate circumstances, include dragging inputs like those discussed with respect to the figures above. As also mentioned, patient record data 224a, such as EMR data, may also be provided to the system 220. Such information may be used to identify the patient 226a, to obtain a gender for the patient, and to identify problems that the patient is facing and treatments the patient is being given 228a, among other things.

The server system 222 may also provide a wide variety of outputs, including outputs that may be used by the users discussed so far, outputs that may be used by other users, and outputs to other sub-systems that are part of a much larger overall healthcare system. For example, various outputs may be provided so as to affect patient EMRs 238, and that can later be viewed on various devices such as laptop, palmtop, netbook, or smartphone computing devices 240. the EMR information may include textual and graphical representations of actions that a user took with respect to a patient, or observations the physician made of the patient. Such observations may be accompanied, for example, by one or more digital images that the user may have taken of the patient. For example, the physician may take a photograph of an injury, such as a laceration to better document in the patient's EMR, the nature and severity of the laceration.

In addition, information may be provided to various administrators 242, such as for review on desktop personal computers 244. For example, administrators may want to "roll up" the information on various procedures and observations made in a system, such as by looking to particular billing codes entered by or on behalf of physicians or nurses. As one example, an administrator may want to identify the rate with which certain procedures are run and compare that rate to comparable other healthcare organizations. Various other uses of such data that is typical of healthcare administrators may also be provided.

Billing information 246 may also be generated by a system that employs server system 222, and may result in a bill 248 being sent to a payor, such as a patient and/or an insurer or managed care program. The billing outputs may, for example, result from a physician tracing a path through groups of icons for objects, actions, and body parts, and thus the occurrence of an associated procedure being registered as having been performed on the relevant patient.

Using these components, the system 220 may provide for simplified input of certain healthcare-related computer interactions. For example, a caregiver may drag cross-wise, wholly from left to right (or downward from top to bottom) across columns of icons, with the icons of a downstream column being affect by what icon was selected in the first column. Such icon selected may be interpreted, in combination, to produce a textual natural language description of the activity that was recorded, perhaps with one or more images or other items being also provided, such as to an EMR.

Figure 3:
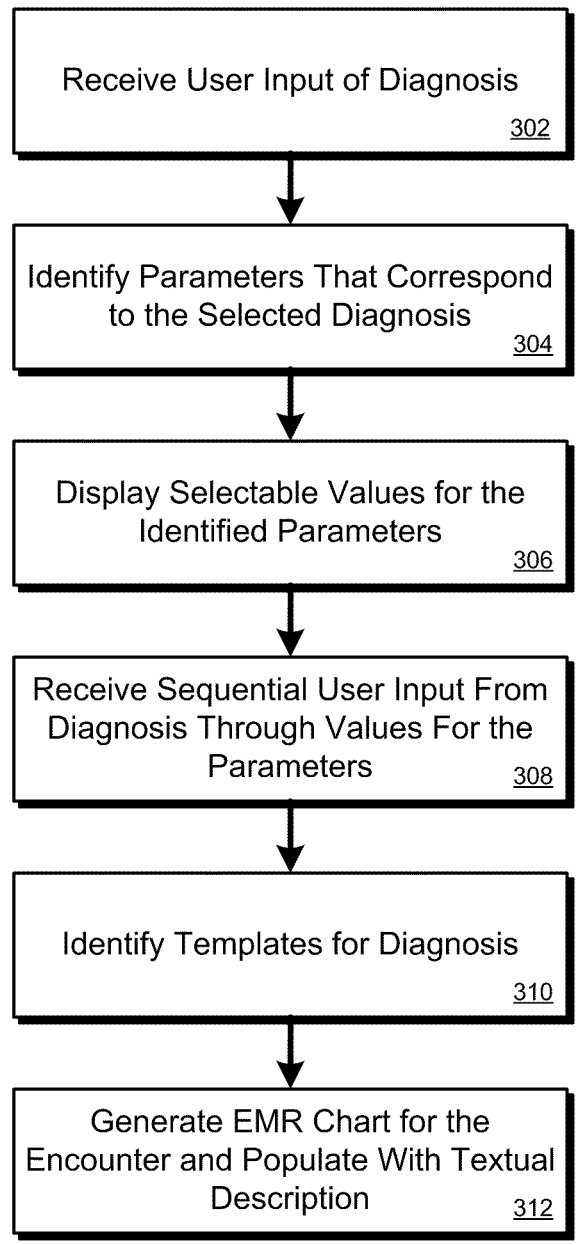
FIG. 3 is a flow chart of a process for generating healthcare notes from caregiver inputs.

FIG. 3 is a flow chart of a process for generating healthcare notes from caregiver inputs. In general, the process relates to a diagnosis-driven input method by which a caregiver identifies a patient diagnosis and then provides detail about the diagnosis, preferably by simple touch input and without a need to type or speak text as part of the input process.

The process begins at box 302, where a system, such as a tablet computer or other computing device, receives a user input of a diagnosis. The user input may be provided in a variety of manners. For example, an initial screen may be displayed that shows icons or menu items for common diagnoses. Such an input mechanisms may have multiple levels so that after a user makes an initial selection, the user is shown more detailed diagnoses. A multi-level approach may be especially appropriate for relatively complex diseases. The organization of the selectable categories may follow a industry standard format or make be custom to a particular group (e.g., cardiologists or pediatricians) or even to a particular user.

At some level of detail, a relatively small number of possible diagnoses may remain—such as 3 to 20 candidates and preferably a number that is small enough to display on a single screen of a computing device. Those diagnoses may then be displayed on icons or other graphical on-screen elements. Each of the elements may also be visually split into multiple selectable areas so that a user can see that selection in one area of an element will have a first effect, and selection in a second area will have a second, different effect.

Figures 4, 5:
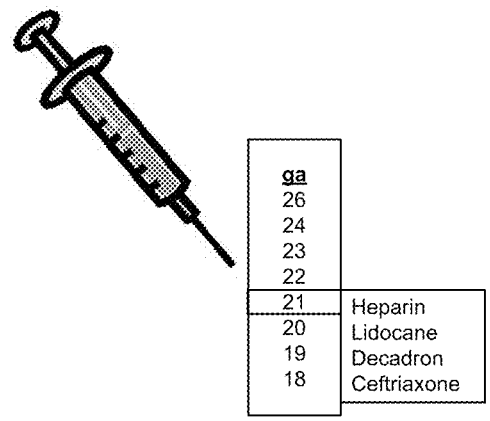
FIG. 4 is an example image for onscreen selections of sub-icons inputs for a healthcare recordkeeping system.
FIG. 5 is an example of a syntax for converting graphical user selections into textual descriptions.

FIG. 4 is an example image for onscreen selections of sub-icon inputs for a healthcare record keeping system. The figure in particular shows an example interface for entering information about provision of a syringe of a drug to a patient. In such an example, the image of the syringe may initially be shown on a touch screen, such as in a modifier column that indicates a treat that was given, and when an object column that was previously selected shows the ailment of the patient for which the shot was given. As the caregiver sweeps his or her finger across the icons and comes to the syringe icon, the box shown to the right of the syringe may pop up and become visible. In this example, the box shows different sizes of syringe. It may be important for a medical record to reflect the size of syringe that was used for various reasons, and it may also affect the amount that the caregiver's employer can be reimbursed for the action. Moreover, identification of the appropriate size of the consumable can assist in operating an automated inventory management system.

In this example, the caregiver has selected a 21 gauge needle by moving his or her finger to the right of the syringe, and then dragging his or her finger downward in the list to 21. Such an action may then cause another pop-up to appear to the right of the first pop-up and aligned with the 21 entry. This second pop-up may show a list of drugs that may be delivered in a particular situation via a 21 gauge needle. Such drugs may include, for example, ceftriaxone, lidocaine, decadron, and heparin, among others. Both lists may be contextual, in that a caregiver may have made a prior selection, such as a selection of a body part, and the sizes and drugs may reflect only those that would normally be given to that body part.

Where a list of parameter values is very long, the caregiver may be provided with a shortened list and an opportunity to scroll through the items in the shortened list. For example, and up arrow and a down arrow may appear adjacent a list and a user may move his or her finger over one of the arrows to scroll. The system may also use multi-touch to permit such manipulation, such as by a user spreading two fingers apart to expand a list of values and pinched the fingers together to contract the list.

Visual indications may be provided with icons that have additional parameters that a caregiver must define. For example, three dots, or an ellipses, may be shown next to icons that require additional input, so that the caregiver can know to expect to be required to provide such additional input as he or she drags across a display. The caregiver may thus slow down when reaching some icons, knowing that he or she cannot easily continue dragging to the next category-based column.

Also, a user's attempt to drag to a next category-based column may be blocked in appropriate circumstances where the user has not entered the appropriate parameter values. For example, an icon may normally drag along with a user's finger as they drag the finger across a screen, so that the user picks up icons while moving, and thereby providing feedback to the user that the icon has been recognized by the system as being selected. Where parameter values need to be entered and they are not, the particular icon can refuse to move along with the user's finger, and the user may thus understand that they need to slide back and see what additional things need to be completed by them.

The pop-up boxes could also appear elsewhere on a display, other than adjacent a particular icon, and could be selected in a different order than that indicated here. For example, a screen could have three category-based columns of icons and a user could drag across all the columns as an initial input. Various boxes may then appear at the bottom of the screen, indicating parameters that a user need to provide for each of the various items that they selected. They may then tap on each parameter in turn and select an appropriate value for it. In building a textual description for the caregiver's action then, the parameters may be inserted as adjectives or adverbs that modify the particular object, e.g., "a 21 gauge heparin syringe."

As another example, where a physician indicates the performance of a laceration repair, the physician may select a laceration and a location of the laceration, and may then select additional modifiers relating the size of suture used, the number of sutures placed, the complexity of repair, and other relevant parameters. As yet another example, where a physician indicates the performance of a physical exam, the physician could start with a location on the body to indicate the area, organ, or system for which information is being provided, and may select modifiers such as the intensity of a murmur, the intensity of abdominal tenderness, and other similar meta data to accompany the main information. Such selections may likewise be constructed into a prose description using semantic rules or other appropriate constructs.

FIG. 5 is an example of syntax for converting graphical user selections into textual descriptions. Such syntaxes may be developed by system designers to match icon entries on a system, and to match understood standards for describing medical actions performed on patients. A system may initially be programmed with a number of such syntaxes, and a customer could acquire (e.g., by download) updated syntaxes over time in a familiar manner, so as to be able to describe new procedures or to comply with regulatory changes. In addition, the rules for syntaxes may also be published, so that customers can easily program their own custom syntaxes.

In the figure, there is shown a syntax for describing the administration of a particular drug to a patient. The first line shows the syntax for a description, where literals in the description are shown outside of brackets and variable are shown inside brackets. The literals are thus "Administered . . . to . . . to treat . . . " While additional values may be defined, the values for the last modifier are shown here. That modifier indicates what was treated. The first definition below the syntax indicates that the modifier may take three forms: laceration, fracture, and sick—though a full definition would have many other options. The laceration option in turn has a number of variable to define the length of the laceration, and the fracture has defined variables to indicate possible types of fractures. Thus, for example, the description could end with " . . . to treat a greenstick fracture." Each of the three main modifiers in description may be defined separately according to a column that they will take in a graphical user interface. Such assignments may be made simply such as by providing a two-column table, in which each row represents a column in the interface and an ID for the relevant modifier that will appear in that column. For example, the three modifiers here may be assigned names in the syntax and their names may be correlated to particular display columns.

Using this defined syntax, user entries on the interface may be readily interpreted into textual representations. For example, as a user (e.g., a critical care worker) drags across the display, they may be shown a column that includes an icon for a laceration, an icon for a fracture, and an icon for a patient who is sick. If they select one of the icons, and parameters that have been defined with the icon may be displayed as pop-up boxes next to the icon, such as requiring a user to move their finger through a list of laceration sizes if they select the laceration icon in a particular column. The user may then move on to the next column in a similar way, and may select appropriate values for the part of a phrase that is represented by that next column. Such mapping may occur in a relatively simple manner when the interface is a graphical equivalent of the sentence that is to be generated, though the columns in the interface my be rearranged to suit a user's taste—e.g., in subject-verb form or in verb-subject form.

Figure 6:
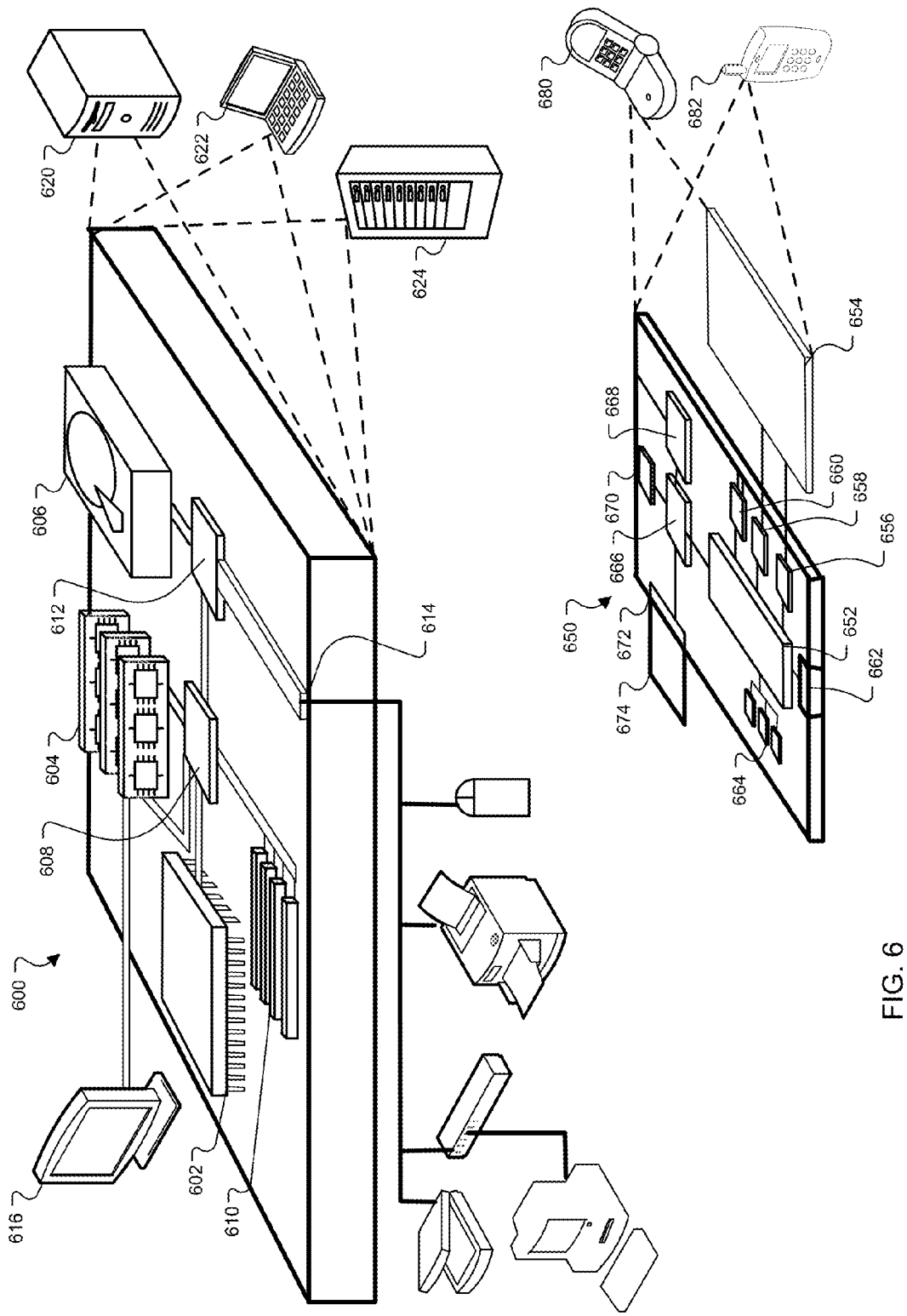
FIG. 6 shows schematic diagrams of a general computer system and a general mobile computing device that may implement the techniques described in this document.

FIG. 6 shows schematic diagrams of a general computer system 500 and a general mobile computing device 550 that may implement the techniques described in this document. Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a volatile memory unit or units. In another implementation, the memory 504 is a non-volatile memory unit or units. The memory 504 may also be another form of computer-readable medium, such as a magnetic or optical disk.

The storage device 506 is capable of providing mass storage for the computing device 500. In one implementation, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 504, the storage device 506, memory on processor 502, or a propagated signal.

The high speed controller 508 manages bandwidth-intensive operations for the computing device 500, while the low speed controller 512 manages lower bandwidth-intensive operations. Such allocation of functions is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed expansion port 514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a micro drive or other device, to provide additional storage. Each of the components 550, 552, 564, 554, 566, and 568, are interconnected using various buses, and several of the components may be mounted on a common motherboard or in other manners as appropriate.

The processor 552 can execute instructions within the computing device 550, including instructions stored in the memory 564. The processor may be implemented as a chipset of chips that include separate and multiple analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD (Thin-Film-Transistor Liquid Crystal Display) or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may be provide in communication with processor 552, so as to enable near area communication of device 550 with other devices. External interface 562 may provide, for example, for wired communication in some implementations, or for wireless communication in other implementations, and multiple interfaces may also be used.

The memory 564 stores information within the computing device 550. The memory 564 can be implemented as one or more of a computer-readable medium or media, a volatile memory unit or units, or a non-volatile memory unit or units. Expansion memory 574 may also be provided and connected to device 550 through expansion interface 572, which may include, for example, a SIMM (Single In Line Memory Module) card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provide as a security module for device 550, and may be programmed with instructions that permit secure use of device 550. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, memory on processor 552, or a propagated signal that may be received, for example, over transceiver 568 or external interface 562.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS (Global Positioning System) receiver module 570 may provide additional navigation- and location-related wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound (e.g., voice messages, music files, etc.) and may also include sound generated by applications operating on device 550.

The computing device 550 may be implemented in a number of different forms, as shown in the figure. For example, it may be implemented as a cellular telephone 580. It may also be implemented as part of a smart phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to smart phones and similar client devices, but other forms of devices may be employed, including jackets for portable devices where the jackets have been provided with some or all of the functionality just described. For example, a jacket for a smart phone could be provided with a pair of metal plates in the jacket to form a large capacitor which may be used to measure force of a user pressing down on a victim's chest during CPR, and such sensed force may be passed to the smart phone, such as through a physical port on the smart phone or a wireless connection. patient monitoring and reporting may also be addressed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for producing electronic health records from graphical inputs by computer users, the method comprising:
receiving, on a graphical user interface of a computer system, a user identification of a diagnosis for a patient, the user identification produced by user selection of a first selectable item from a plurality of selectable items that are each indicative of diagnoses and that are displayed in a first zone on the graphical user interface;

identifying, with the computer system and in response to receiving the user selection of the diagnosis, a plurality of parameters that each correspond to and characterize the diagnosis;

displaying in a second zone that is spatially separated from the first zone on the graphical user interface and in response to identifying the plurality of parameters, a plurality of selectable values for each of multiple ones of the plurality of parameters, wherein the first and second zones have edges that are adjacent to each other that do not overlap each other;

receiving, by the computer system and from the user, sequential user selections that represent multiple particular ones of the values from the plurality of parameters that each correspond to and characterize the diagnosis; and generating an electronic health record representation that represents a particularized version of the identified diagnosis with text for values selected by the user from the parameters that correspond to and characterize the diagnosis, wherein the representation is generated by applying a syntax to the selected diagnosis and values for the selected diagnosis along with text not selected by the user, to generate a natural language description from multiple sub-sentence clauses after the user identification and the sequential user selections are received, wherein, once the user identification of the diagnosis for the patient and the sequential user selections of the values for the one or more parameters that correspond to and characterize the diagnosis have been selected, the first selectable item that is representative of the diagnosis is displayed along with the selected values of parameters that correspond to and characterize the diagnosis as a visually-identified group, for review by the user, and wherein the user can move from any of the plurality of selectable items that are representative of a diagnosis in the first zone to any of the plurality of selectable values of parameters that correspond to and characterize the diagnosis in the second zone without moving over any other item in the first zone or any other value in the second zone.

2. The method of claim 1, wherein the values for the modifiers are displayed adjacent to a representation of the identified diagnosis and are selected from user-specific files that indicate preferred values for particular users.

3. The method of claim 2, wherein receiving the sequential selections comprises receiving user selections as a user gesture in a single direction across the user interface from the identification of the diagnosis through the selections of the values by the user changing or accepting initially-displayed values.

4. The method of claim 1, wherein at least some of the values are displayed as selectable icons and at least some of the values are displayed as alphanumeric characters.

5. The method of claim 1, wherein the user indication of a diagnosis comprises an identification by the user of finding that is less than a complete diagnosis.

6. The method of claim 1, further comprising, after receiving a selection of a first value of a first modifier, automatically changing values displayed for a second modifier in dependence on the selected first value.

7. The method of claim 1, wherein the user identification of a diagnosis is received on an icon having multiple contact zones, and a diagnosis type is selected from multiple different diagnosis types based on a determination of which contact zone for the icon is selected by the user.

8. The method of claim 1, wherein receiving sequential user selections comprises receiving a pair of user selections for an item, and further comprising undoing a first user selection of the item upon receiving a second user selection of the item.

9. The method of claim 1, further comprising applying a syntax to populate a data record for the diagnosis by:
identifying at least a modifier and a value selected for the modifier; and
constructing a set of descriptive medical observations in an electronic document from a template or tree, and adding text for the modifier and the selected value to the template or tree.

10. The method of claim 9, wherein constructing a set of descriptive medical observations comprises creating a prose sentence for a health record.

11. The method of claim 1, further comprising identifying a patient who corresponds to the user selections, and adding a set of descriptive medical observations to an electronic medical record for the identified patient.

12. The method of claim 1, further comprising receiving a description of a patient complaint, determining one or more diagnoses that address the complaint, and displaying representations of the one or more diagnoses on the graphical user interface.

13. A computer-implemented system for producing electronic health records from inputs by caregivers in a graphical user interface, the system comprising:
one or more processors; and
one or more non-transient storage devices operably connected to the one or more processors and storing instructions, that when executed, implement features comprising:
a display controller configured to generate data for displaying selectable icons that represent patient diagnoses, and for displaying values for parameters that characterize the diagnoses, and that are dependent on, a user-selected diagnosis, wherein the selectable icons are displayed in a zone that is spatially separated from a zone in which the values for parameters that characterize the diagnoses are displayed, and wherein selection of each icon results in an identification of and display of values for a parameter that is determined to characterize a diagnosis for the particular selected icon;
an input processor configured to receive user selections of the diagnosis and values and to identify parameters that characterize the user-selected diagnosis; and
a description builder programmed to apply syntactical rules based on the selected diagnosis and selected values to produce prose of a description for a medical action represented by the selected diagnosis and values, wherein the description is constructed from multiple sub-sentence clauses that together describe a user selection of an icon for a diagnosis and values for the diagnosis,
wherein, once a user has selected an icon that represents a particular diagnosis and values for parameters that characterize the particular diagnosis, the selected icon is displayed along with the selected values as a visually-identified group, for review by the user, and
wherein the a user can move from any of the plurality of icons to any of the plurality of selectable values without moving over any other item in the zone in which the icons are displayed or the zone in which the values for modifiers are displayed.

14. The system of claim 13, wherein the user selections comprise sequential selections on a touchscreen that identify the selected diagnosis followed by the modifiers.

15. The system of claim 13, wherein the display controller is configured to display an icon having multiple contact zones and, and a diagnosis type is selected from multiple different diagnosis types based on a determination of which contact zone for the icon is selected by the user.

16. The system of claim 13, wherein the description builder is further programmed to apply a syntax to populate a data record for the diagnosis by:
   identifying at least a modifier and a value selected for the modifier; and
   constructing a set of descriptive medical observations in an electronic document from a template or tree, and adding text for the modifier and the selected value to the template or tree.

17. The system of claim 13, wherein the description builder is programmed to receive a description of a patient complaint, determining one or more diagnoses that address the complaint, and displaying representations of the one or more diagnoses on the graphical user interface.

18. One or more tangible, non-transitory computer-readable storage media having stored thereon instructions, that when executed by one or more processors, perform operations comprising
   receiving, on a graphical user interface of a computer system, a user identification of a diagnosis for a patient, the user identification produced by user selection of a first selectable item from a plurality of displayed selectable items that are each indicative of diagnoses and that are displayed in a first zone on the graphical user interface;
   identifying, with the computer system and in response to receiving the user selection of the diagnosis, a plurality of parameters that each correspond to and characterize the diagnosis;
   displaying in a second zone that is spatially separated from the first zone on the graphical user interface and in response to identifying the plurality of parameters, a plurality of selectable values for each of multiple ones of the plurality of parameters, wherein the first and second zones have edges that are adjacent to each other that do not overlap each other;
   receiving, by the computer system and from the user, sequential user selections that represent multiple particulars ones of the values from the plurality of parameters that each correspond to and characterize the diagnosis; and
   generating an electronic health record representation that represents a particularized version of the identified diagnosis with text for values selected by the user from the parameters that correspond to and characterize the diagnosis, wherein the representation is generated by applying a syntax to the selected diagnosis and values for the selected diagnosis along with text not selected by the user to generated a natural language description from multiple sub-sentence clauses after the user identification and the sequential user selections are received,
   wherein, once the user identification of the diagnosis for the patient and the sequential user selections of the values for the one or more parameters that correspond to and characterize the diagnosis have been selected, the first selectable item that is representative of the diagnosis is displayed along with the selected values of parameters that correspond to and characterize the diagnosis as a visually-identified group, for review by the user, and
   wherein the user can move from any of the plurality of selectable items in the first zone to any of the plurality of selectable values in the second zone without moving over any other item in the first zone or any other value in the second zone.

19. The one or more media of claim 18, wherein receiving the sequential selections comprises receiving user selections as a user gesture in a single direction across the user interface from the identification of the diagnosis through the selections of the values by the user changing or accepting initially-displayed values.

20. The one or more media of claim 18, wherein the operations further comprise applying a syntax to populate a data record for the diagnosis by:
   identifying at least a modifier and a value selected for the modifier; and
   constructing a set of descriptive medical observations in an electronic document from a template or tree, and adding text for the modifier and the selected value to the template or tree.

* * * * *